US006684682B2

(12) United States Patent
Stemmle et al.

(10) Patent No.: US 6,684,682 B2
(45) Date of Patent: Feb. 3, 2004

(54) JOGGER SYSTEM HAVING A MAIL COMPRESSION CAPABILITY THEREIN

(75) Inventors: Denis J. Stemmle, Stratford, CT (US); Eric A. Belec, Southbury, CT (US); Robert J. Allen, Shelton, CT (US); Michael M. Farrell, Beacon Falls, CT (US); Jeffrey A. Gateman, Gales Ferry, CT (US); Thomas M. Lyga, Southbury, CT (US); Edward C. Miller, Woodbridge, CT (US); John F. Zajac, Garnerville, NY (US)

(73) Assignee: Pitney Bowes Inc., Standford, CT (US)

( * ) Notice: Subject to any disclaimer, the term of this patent is extended or adjusted under 35 U.S.C. 154(b) by 34 days.

(21) Appl. No.: 10/035,979

(22) Filed: Dec. 24, 2001

(65) Prior Publication Data

US 2003/0115931 A1 Jun. 26, 2003

(51) Int. Cl.$^7$ ............................. B65B 43/30; B26D 1/28
(52) U.S. Cl. ........................... 73/23.2; 73/37; 53/381.6; 53/386.1
(58) Field of Search .................. 73/23.2, 31.02, 73/37, 864.41, 864.83, 864.85; 422/83, 88, 386.1; 53/381–386

(56) References Cited

U.S. PATENT DOCUMENTS

| 3,828,634 | A |   | 8/1974  | Luperti ........................ 83/94 |
| 4,016,708 | A | * | 4/1977  | DeHart ..................... 53/381 R |
| 4,045,997 | A | * | 9/1977  | Showalter et al. ........... 73/23.2 |
| 4,964,309 | A | * | 10/1990 | Jenkins .................... 73/864.81 |
| 5,268,302 | A | * | 12/1993 | Rounbehler et al. .......... 436/96 |
| 5,585,575 | A | * | 12/1996 | Corrigan et al. .......... 73/863.71 |
| 5,915,268 | A | * | 6/1999  | Linker et al. ................. 73/23.2 |
| 6,047,588 | A | * | 4/2000  | Danilychev ................. 73/23.2 |
| 6,228,657 | B1 | * | 5/2001 | Genovese et al. ........... 436/167 |
| 6,375,697 | B2 | * | 4/2002 | Davies ........................ 55/340 |

* cited by examiner

Primary Examiner—Helen Kwok
Assistant Examiner—David J. Wiggins

(57) ABSTRACT

A method for expelling air out of mailpieces includes the steps of creating a stack of the mailpieces; cutting an opening in at least some of the mailpieces; jogging the stack of mailpieces; and subjecting the stack of mailpieces to at least one compression/decompression cycle during the jogging step thereby expelling air out of the at least some of the mailpieces through their corresponding openings. A jogger system incorporates the structure for accomplishing the method.

20 Claims, 10 Drawing Sheets

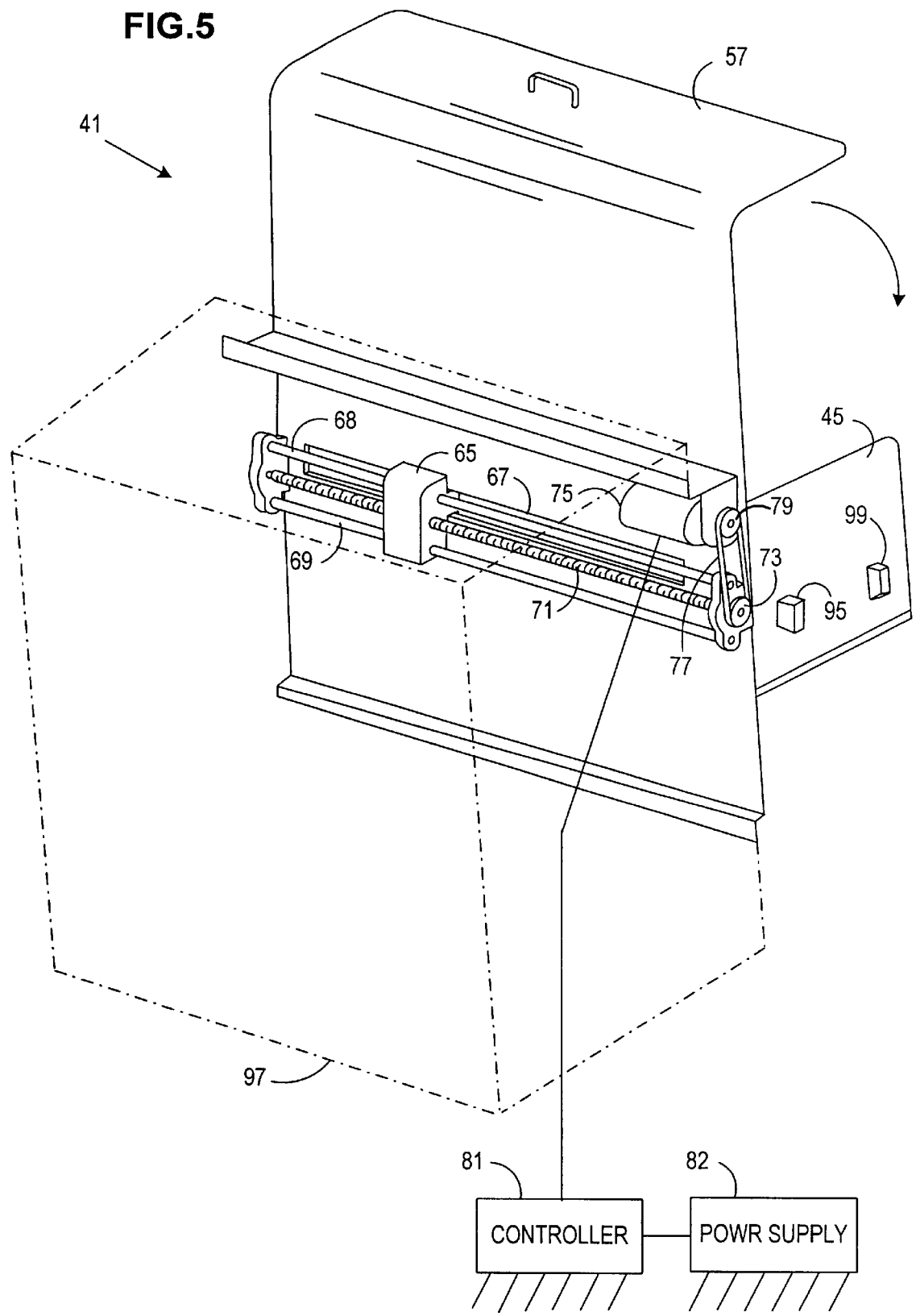

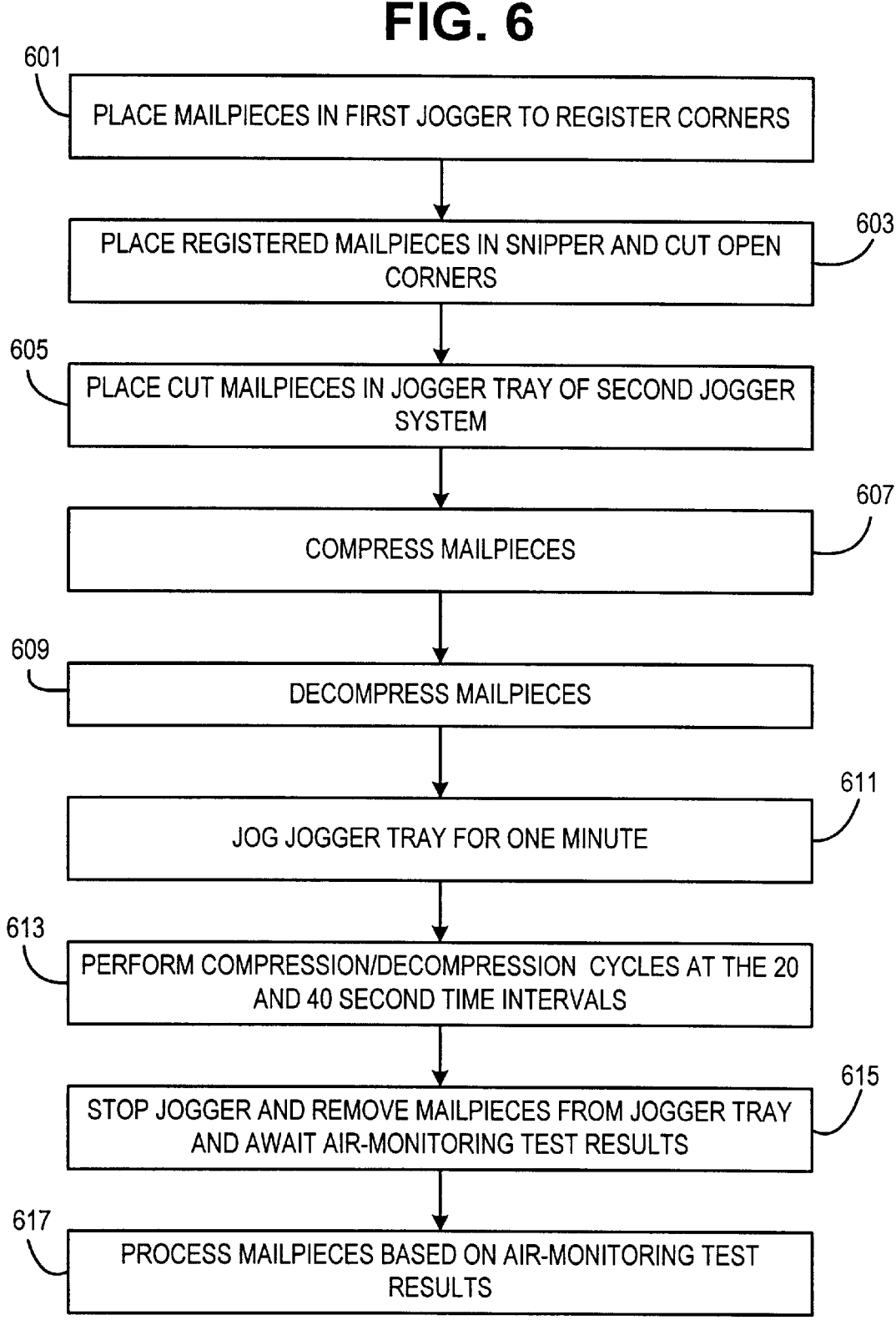

US 6,684,682 B2

JOGGER SYSTEM HAVING A MAIL COMPRESSION CAPABILITY THEREIN

BACKGROUND OF THE INVENTION

The instant invention relates to systems for expelling powder materials from mailpieces, and more particularly to a jogger system that compresses mailpieces while performing a jogging function.

Recent events have led to the realization that unscrupulous individuals may attempt to use the postal delivery system as a vehicle for spreading terrorism. These individuals have, for example, contaminated mailpieces with biological agents (such as anthrax) and distributed such mailpieces to targeted locations via the postal service. While the extent of damage that may occur by using mailpieces as a carrier of biological agents has yet to be determined, the potential for significant health risks is clear. Accordingly, increased efforts have been set forth toward the development of systems and processes that may be effective in detecting contaminated mailpieces within the postal delivery system prior to delivery to their final destination.

One such proposed system involves snipping the corner off every mailpiece (to create an opening at the corner of the envelope), placing the snipped mailpieces in a jogger system, operating the jogger system for approximately 3 minutes, pulling ambient air through the jogger system, monitoring the pulled air with two systems (one to test particle size and one to capture powder in a filter for subsequent lab testing of the material captured), then banding the mailpieces in a conventional banding machine to squeeze air out of the mailpieces, and finally sampling the air from the banding operation with the above two air-monitoring systems to determine the presence and nature of any powder materials prsent in the airflow. The air pulled through the individual workstations in this process is moved through a HEPA filter and vented outside the work area. Operation of this system is a time consuming process, with manual steps taken between each operation.

In the proposed system, once the air-monitoring filter has been tested for the presence of a biological agent, the mailpieces are unbanded and moved to a separate area for sorting and final distribution if the results of testing are negative. If a biological agent is detected however, the facility is shut down until decontamination can be performed.

One of the problems with the proposed system is the time required for the banding/unbanding operation. The value of the banding operation is not in the band that is placed around the mailpieces, but rather in the compression of the mailpieces that occurs during banding. The compression step serves to expel air from the mailpieces. In the event that a biological powder material is present in the mailpieces, it is carried with the expelled air and subsequently detected by the air-monitoring apparatus. Accordingly, if the banding/unbanding operation could be eliminated, the system would have a higher throughput and would benefit from a cost and complexity standpoint. By eliminating the banding/unbanding operation, the banding equipment and the ductwork associated with it can be eliminated. Also, the volume of air that would be required to be pulled through the entire system would be decreased thereby permitting the use of smaller vacuum sources thereby reducing costs.

SUMMARY OF THE INVENTION

A method for expelling air out of mailpieces includes the steps of creating a stack of the mailpieces; cutting an opening in at least some of the mailpieces; jogging the stack of mailpieces; and subjecting the stack of mailpieces to at least one compression/decompression cycle during the jogging step thereby expelling air out of the at least some of the mailpieces through their corresponding openings. A jogger system incorporates the structure for accomplishing the method.

BRIEF DESCRIPTION OF THE DRAWINGS

The accompanying drawings, which are incorporated in and constitute a part of the specification, illustrate a presently preferred embodiment of the invention, and together with the general description given above and the detailed description of the preferred embodiment given below, serve to explain the principles of the invention.

FIG. 5 shows a rear view of the jogger system of FIG. 4;

FIG. 6 is a flowchart showing the operation of the jogger system of FIG. 4 as used in an inventive detection system;

DETAILED DESCRIPTION OF THE PREFERRED EMBODIMENT

Figure 1:
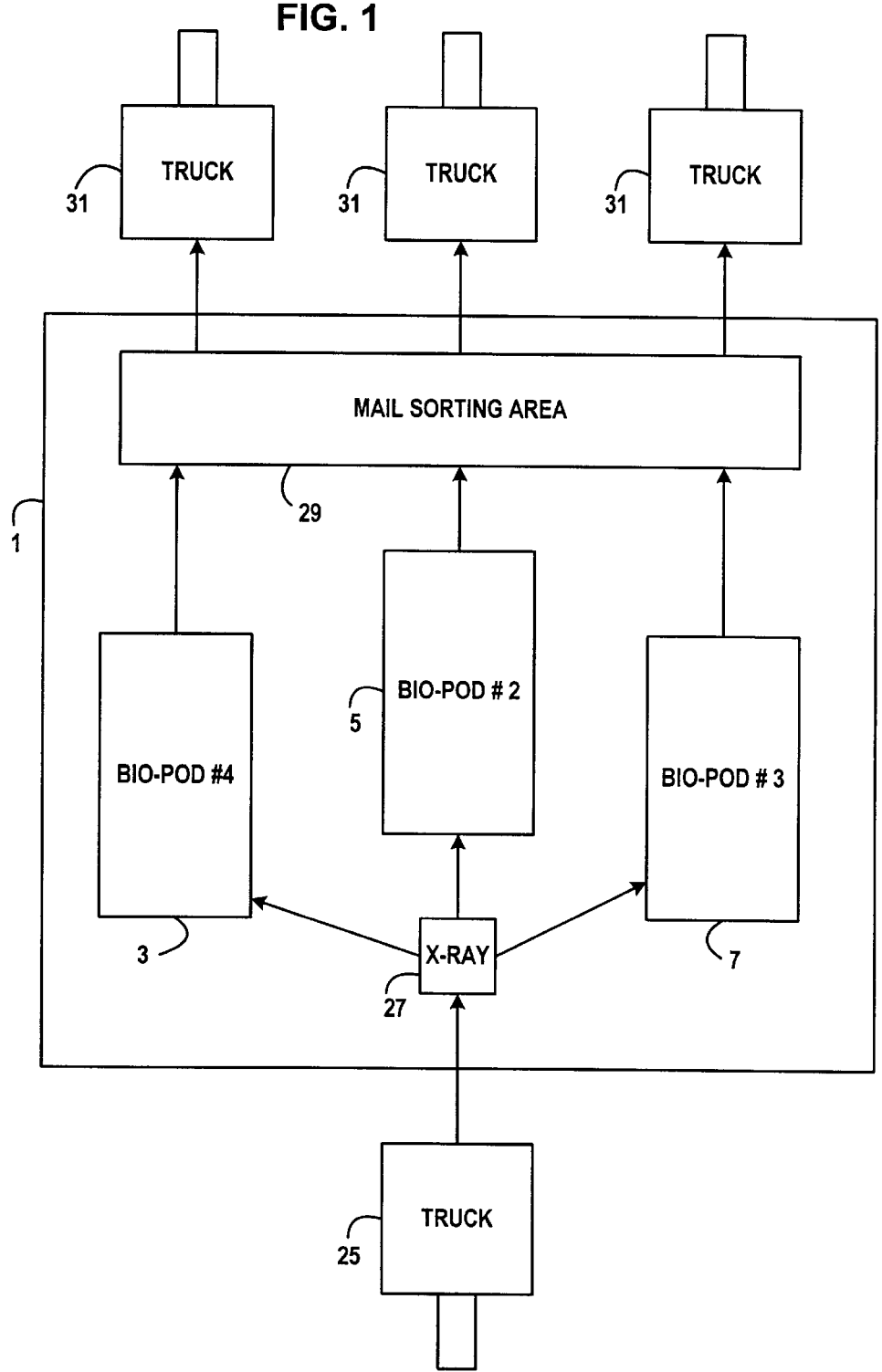
FIG. 1 is a schematic diagram of a known warehouse mail processing facility.

FIG. 1 shows a conventional warehouse facility 1 containing three bio-pods 3, 5, and 7 that are used to detect biological agents contained in mailpieces being processed through the warehouse facility 1. Each of the bio-pods 3, 5, and 7 contain one or more of the biological agents detection system 9 shown in FIG. 2. The detection system 9 includes a conventional jogger system 11, a corner snipper 13 (such as the "Corner Rounder", model 50P sold by Lassco Products), a vacuum and HEPA filter system 15, a banding mechanism 17, first and second air-monitoring systems 19, 21 and associated ductwork 23 that connects each of the work stations 11, 13, 17, 19, and 21 to the vacuum and HEPA filter system 15.

Figure 2:
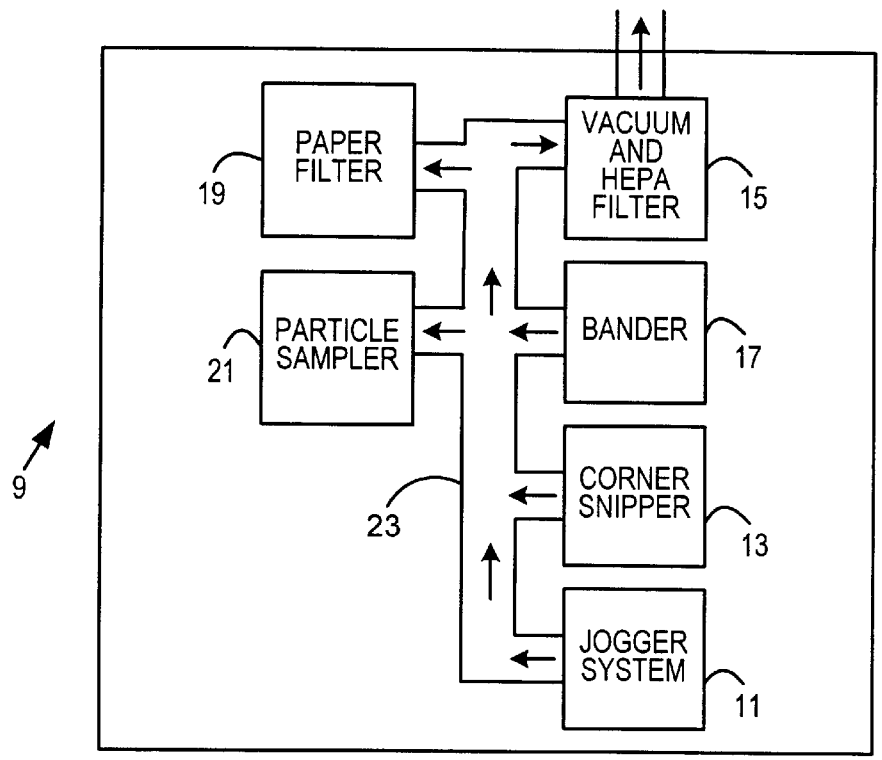
FIG. 2 is a schematic diagram of the detection system used in the warehouse facility of FIG. 1.
Figure 3:
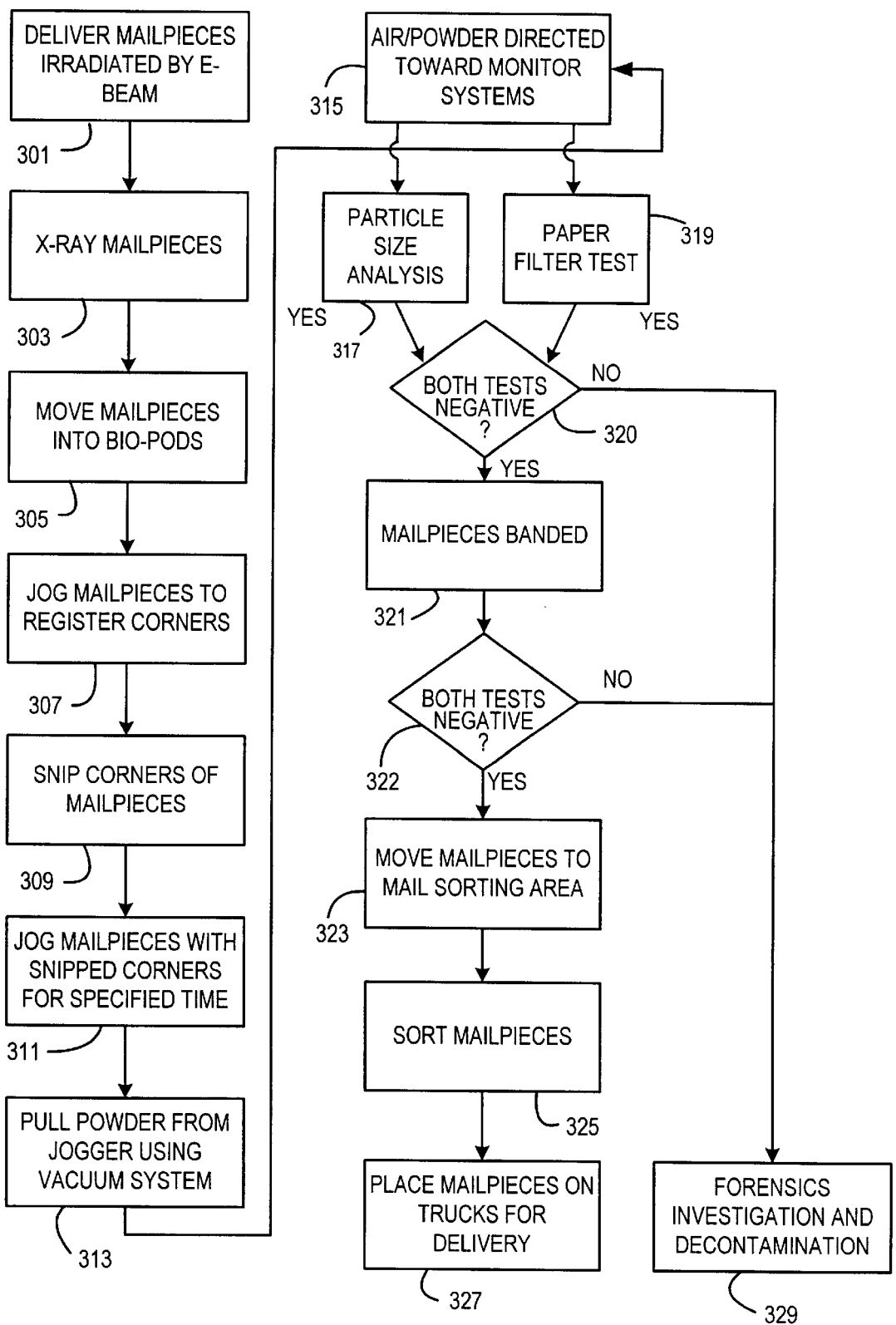
FIG. 3 is a flowchart of the processing of mailpieces in the warehouse mail processing facility.

The operation of the bio-pods 3, 5, and 7 will now be described in connection with FIGS. 1, 2, and 3. First, mailpieces are delivered by a truck 25 to the warehouse facility 1 for processing. The mailpieces may have previously been irradiated with an e-beam in an attempt to destroy any biological agents that may have been present (301). Upon delivery to the warehouse 1, the mailpieces are first passed through an X-ray machine 27 in an attempt to detect incendiary or explosive devices and to segregate questionable items accordingly (303). The mailpieces are then moved into one of the bio-pods 3, 5, and 7 (305). The mailpieces are then placed in the jogger system 11 and jogged (vibrated) in a known manner to register the corners of a batch (typically approximately 1" thick) of mailpieces (307). After registration, the batch of mailpieces are placed in the known corner snipper 13 in their registered orientation so that the snipper 13 can snip off one corner of each of the mailpieces in a single cutting motion (309).

The small batches of snipped mailpieces are then combined into larger batches of approximately 8–12" in thickness and reloaded into the jogger system 11 and jogged for approximately 3 minutes (311). During this jogging period the snipped corners are registered and if any biological agent powder materials are present in the mailpieces it is expected that the powder materials will leave the mailpiece through the opened corners. The jogger system 11 is enclosed and connected to the ducting 23 such that some of the powder material will be pulled from the jogger 11 toward the vacuum system 15 (313). As the powder material flows toward the vacuum system 15, portions of it are directed to the first and second air monitoring systems 19, 21 (315). The second monitoring system 21 detects the particle size of any powder material that is present and performs a particle size analysis. Based on the particle size analysis, the potential presence of a biological hazard may be indicated (317).

The first monitoring system 19 includes a paper filter that collects portions of any powder material that is present in the airflow being deflected therethrough. The paper filter is removed, for example, once per day and sent to a lab to test for the presence of biological agents (319). If the results of steps 317 and 319 are both negative (320) the normal processing of the mailpieces 87 continues.

After the jogging process is completed, the batch of mailpieces is sent to the known banding system 17 where the batch of mailpieces is compressed during banding (321). The compressing step forces the air inside the mailpieces to be ejected within the enclosed banding system 17. The vacuum system 15 draws the ejected air from the banding system 17 through the ductwork 23 such that portions of the ejected air will be sampled at the first and second air-monitoring systems 19, 21 as discussed above (322). If during the above processing of the mailpieces through the bio-pods 3, 5, and 7 no biological agents have been detected, the mail is moved from the bio-pods 3, 5, 7 to a mail sorting area 29 (323). The banded batches of mailpieces are unbanded and sorted for delivery by their destination zipcodes (325). The batches of mailpieces are then placed on trucks 31 to continue being processed through the normal mailpiece distribution system (327).

In practice, the results of the lab tests on the paper filter takes about 24 hours. Accordingly, two of the three bio-pods 3, 5, and 7 are used on alternate days for processing mailpieces while the third bio-pod remains unused. If however, a biological agent is detected in one of the bio-pods based on filter testing and particle size analysis, the mailpieces in that bio-pod remains quarantined until authorities complete a forensics investigation and perform any required decontamination of the contaminated bio-pod (329). In the meantime, the processing of mailpieces continues in the manner described above using the other two bio-pods.

Figure 4:
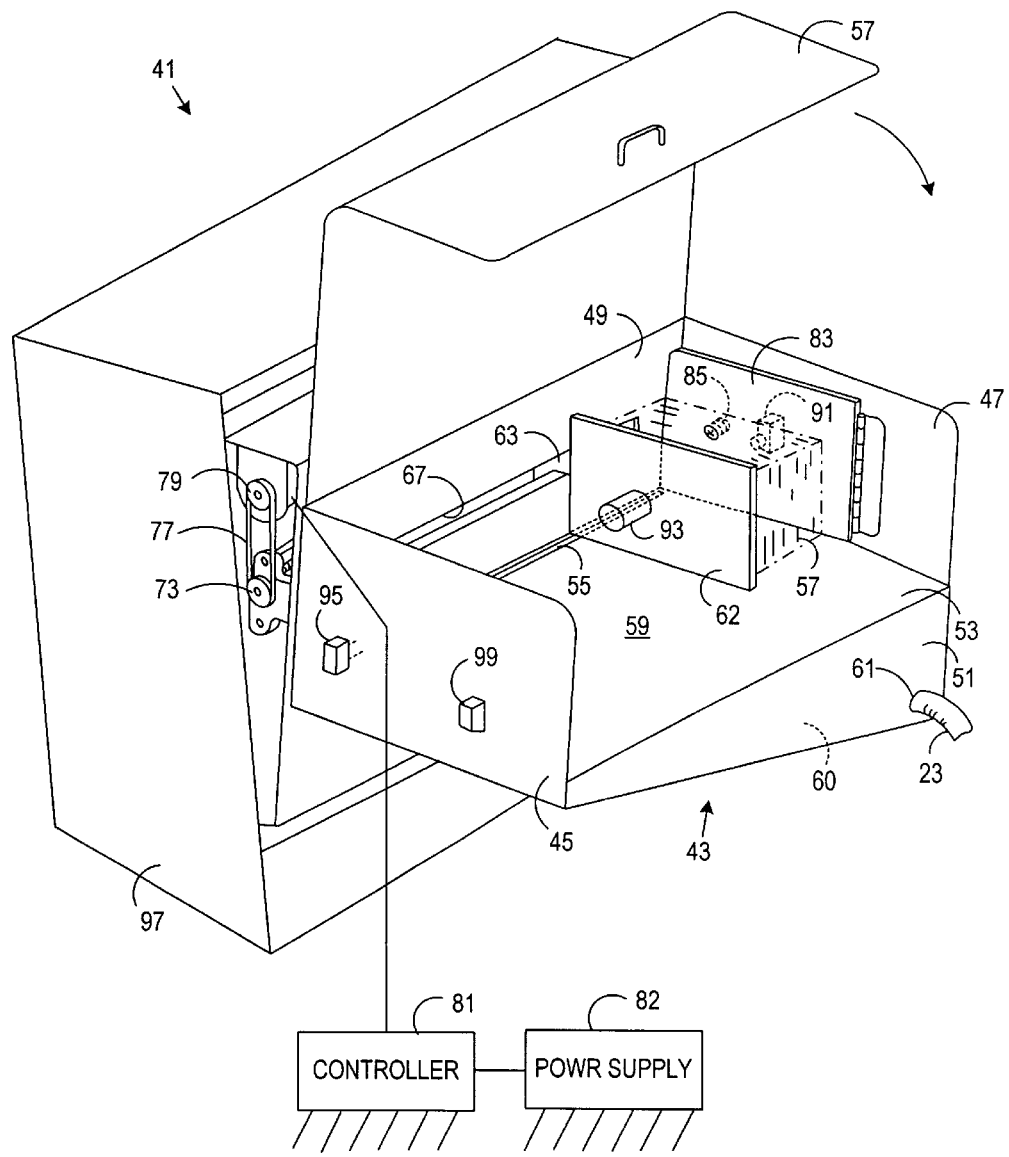
FIG. 4 shows a perspective view of an inventive jogger system.

The instant inventors have eliminated the need for the banding machine 17 by inventing the jogger system 41 shown in FIGS. 4 and 5. The jogger system 41 includes a housing 43 (also referred to herein as a jogger tray) defined by two sidewalls 45, 47, a rear wall 49, a front wall 51, and a platform 53. The platform 53 does not extend to the rear wall 49 such that an opening 55 exists, between the rear wall 49 and the platform 53, that runs the full length of the platform 53. The jogger tray 43 also includes a cover 57 that is hinged to back wall 49 for movement between the open position shown in FIGS. 4 and 5 and a closed position. In the closed position, the cover 57 together with the side walls 45, 47 and rear wall 49 define a first enclosed chamber 59. Further, a second enclosed chamber 60 is defined by the space created between the bottom of the platform 53, side walls 45, 47, rear wall 49 and front wall 51. Additionally, front wall 51 has an opening 61 therein which is in operative communication with the ductwork 23 to permit air to be pulled through opening 55 into the second chamber 60 and thereafter pulled out from the second chamber by the vacuum and HEPA filter system 15.

In addition to the jogging tray 43, a paddle 62 is mounted for movement between the side walls 47 and 45. The paddle 62 is mounted on an arm 63 of a bracket 65. The arm 63 passes through a slot 67 in the back wall 49. The bracket 65 is mounted on two guide rods 68, 69 and a lead screw 71. The lead screw 71 has a pulley 73 attached at one end thereof and is operatively connected to a motor 75 via an endless belt 77 that extends around the pulley 73 and a second pulley 79 connected to a shaft of the motor 75. Accordingly, as the bi-directional motor 75 is energized, the lead screw 71 is forced into rotation causing a corresponding movement in the bracket 65 along the lead screw 71 and the guide rods 68, 69. A controller 81 is operatively connected to the motor 75 to control the supply of power from a power source 82 to the motor 75. The controller 81 therefore controls the movement of the paddle 62 between the side walls 45, 47. The controller 81 and power source 82 are typically mounted on a table (not shown) upon which the jogging system 41 is placed.

A hinged plate 83 is connected to side wall 47 and biased away from the side wall 47 by a spring 85. Mailpieces 87 are positioned between the paddle 62 and plate 83 such that the snipped lower corner of each mailpiece is placed near rear wall 49. Thus, the opening in the mailpieces at the snipped corners are disposed over the opening 55. Once the mailpieces are placed between the paddle 62 and the plate 83, the controller 81 controls the motor 75 to move the paddle 62 toward the plate 83 to compress the mailpieces 87. A switch 91, mounted on side wall 47, is activated when plate 83 is forced by the movement of paddle 62 into the mailpieces 87 to contact the switch 91. The switch 91, upon activation, sends a signal to the controller 81. Upon receipt of the switch signal, the controller 81 stops the movement of the paddle 62 into the mailpieces 87 and retracts the paddle 62 a small distance thereby allowing the mailpieces 87 to decompress.

When the mailpieces 87 are to be removed, the controller 81 will activate the motor 75 to move the addle 62 toward side wall 45. A projection 53 on paddle 62 will contact and activate a second switch 95 on side wall 45. Upon activation of the second switch 95, signal is sent to the controller 81. Upon receipt of the signal from the second switch 95, the controller 81 stops the movement of the paddle 62.

The entire jogger tray 43 is mounted to a conventional jogging device shown schematically at 97. The jogging device 97, when activated, will vibrate the entire jogging tray 43 such that the mailpieces 87 become registered against the rear wall 49 and the platform 53 as shown. To assist in the registration process, the entire jogging tray 43 is mounted to the jogging device 97 such that platform 53 is angled downward toward both the rear wall 49 and the side wall 47.

The jogging device 97 can be one of many conventional devices that can vibrate objects attached thereto using mechanical or electromagnetic techniques. Examples of known joggers include the "Quiet Jog" sold by the Omation Division of Opex® Corporation and the "LasscoJog"— model LJ-4 sold by Lassco Products. It is contemplated by the inventors that any known jogging device that can be adapted to have the jogging tray 43 mounted thereto can be used.

Figure 7:
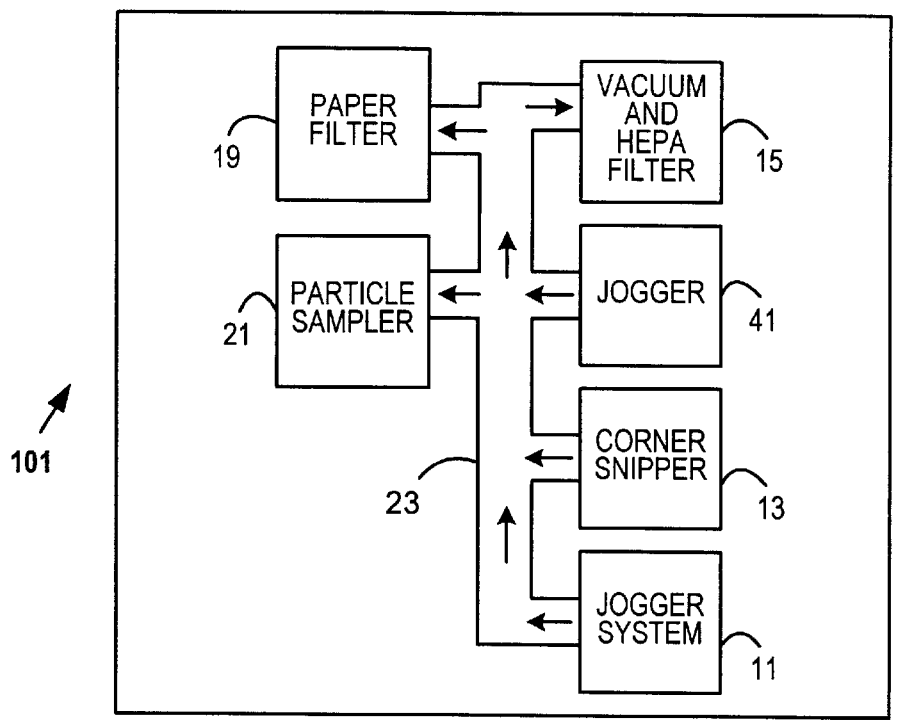
FIG. 7 is a schematic diagram of the inventive detection system.

Referring to FIGS. 6 and 7, an inventive detection system 101 is shown incorporating the inventive jogger system 41. The detection system 101 has eliminated the need for a banding device 17 because the jogger system 41 includes compression apparatus as described above. In operation, the mailpieces 87 are placed in a conventional jogger system 11 in order to register the corners of the mailpieces 87 over the opening 55 as discussed above (601). The registered mailpieces 87 are then placed in the corner snipper 13 where their corners are cut open (603). The mailpieces 87 with the cut corners are placed in the jogger tray 41 of the jogger system 41 (605). Next a start button 99 is depressed by the operator which signals the controller that compression of the mailpieces is required. The controller 81 energizes the motor 75 to move the paddle 62 from the home position at switch 95 into contact with the mailpieces 87. The paddle 62 is driven until the switch 91 is activated by movement of the plate 83. At this point in time the mailpieces 87 are in a compressed state (607). Upon receipt of the signal from activated switch 91, the controller 81 causes the motor 75 to retract the paddle 62 a small distance such that the mailpieces 87 decompress by filling with air (609). At this point in time the jogger device 97 is switched on (in a conventional manner) to vibrate the jogger tray 43 for a predetermined period of time, such as one minute (611). The controller 81 is designed to move the paddle 62 to perform a compression operation as described above once every 20 seconds. Accordingly, during the vibrating of the jogger tray 43 the mailpieces 87 will be compressed and decompressed at the 20 second and 40 second time intervals during the one minute vibration period (613). Once the vibrating cycle is finished (jogger device) stopped, the paddle 62 returns to the home position and the mailpieces 87 are removed and set aside until the results of the testing at the first and second air-monitoring systems 19, 21 has been completed (615). The processing of the mailpieces 87 subsequent to obtaining the air-monitoring tests are tle same as shown in FIG. 6 (617). If the testing is negative steps 323, 325, and 327 are performed except that the removal of the band from the mailpieces 87 is not required. If the testing is positive step 329 is performed.

The compression of the mailpieces 87 during the vibration cycle allows air inside the mailpieces 87 to be expelled through their opened corners. If powdered biological material is present inside the mailpieces 87, some of the biological powder will be carried with the expelled air. This powder will fall through the opening 55 and into the second chamber 60. The vacuum and HEPA filter system 15 will draw the powder material through the ductwork 23 such that most of it will be captured by the HEPA filter system 15 while some of it will flow to the air-monitoring systems 19, 21. Once the paddle 62 is retracted such that the mailpieces 87 are allowed to decompress, biological powder can still pass through the corner opening of the mailpieces 87 and through the opening 55 during the vibration of the jogging tray 43.

The advantage of performing multiple compression/decompression cycles during the vibrating cycle is that during the compression cycle there is a greater probability that any powder residing in the mailpieces 87 will be expelled out of the mailpieces 87 through their opened corners than during the period where the mailpieces 87 are not compressed. Naturally, while a specific number of compression/decompression cycles have been discussed, the instant invention contemplates that any number of compression/decompression cycles can be used during the jogging period and the frequency and duration of such cycles can be adjusted as well. Additionally, the jogging period can be shorter or longer than 1 minute.

In FIG. 7, two jogger systems 11 and 41 are used to improve the overall efficiency of the detection system 101. That is, since the initial registration jogging function (step 601) and the snipping operation (step 603) are likely to take longer than the jogging and compression operation (steps 611, 613), the use of a dedicated registration jogger 11 will improve mailpiece throughput. However, the instant invention could be implemented using only the jogger 41 which would be used in a first instance to register the mailpieces 87 prior to the snipping operation and in a second instant be used for the compression/decompression cycling for expelling powder from the mailpieces 87.

Figure 8:
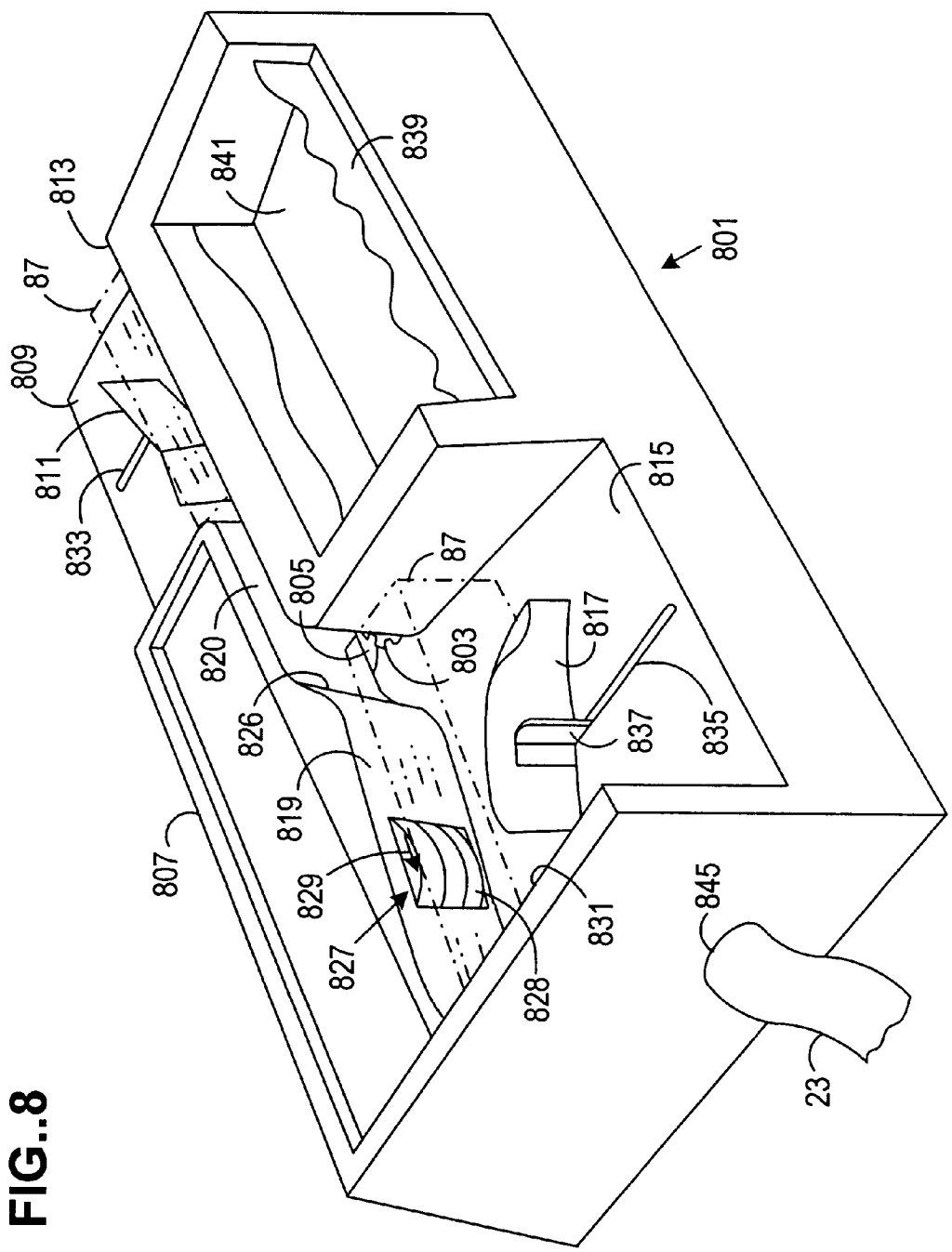
FIG. 8 is a perspective view of the inventive mailpiece opening system.

By way of reference to FIGS. 8–11, a description of an inventive envelope cutting system that can be used in lieu of the corner snipper 13 shall be described. FIG. 8 shows a Pitney Bowes Inc.® 1250 mail opening system 801 that has been modified to include the inventive cutting system that includes a pair of cutter wheels 803, 805. The mail opening system 801 further includes a housing 807 having an envelope infeed platform 809. An envelope retainer 811 is located on infeed platform 809 and is spring loaded towards an infeed envelope guide wall 813.

Figure 9:
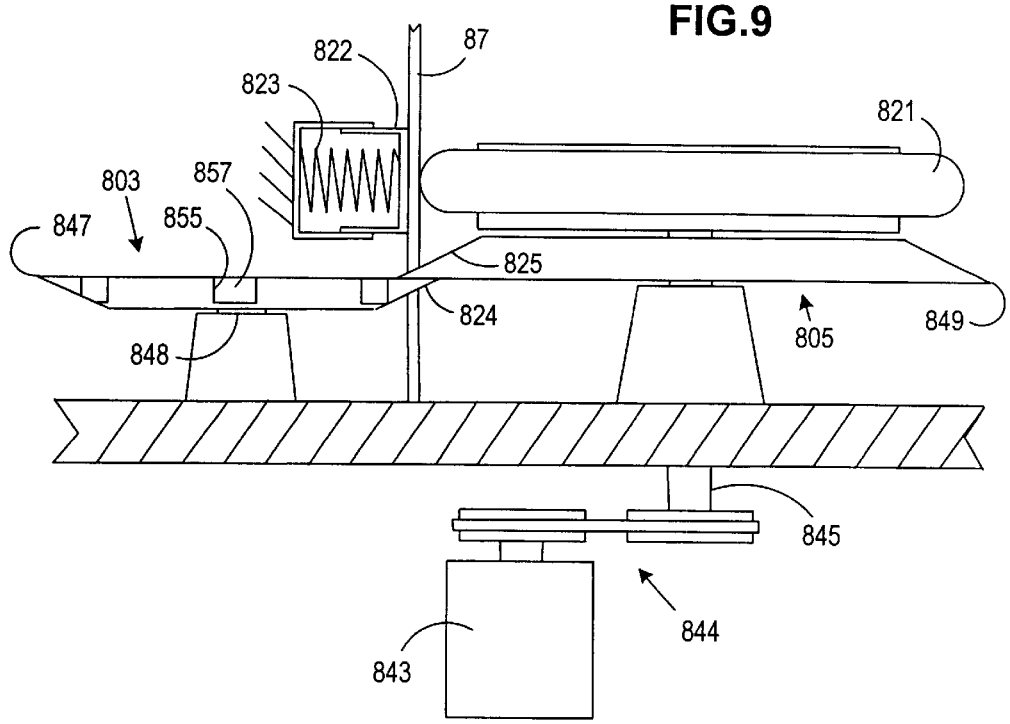
FIG. 9 is a view showing the mailpiece transport and cutter wheel drive system of FIG. 8.

An envelope outfeed platform 815 is provided with an envelope retainer 817 in the form of a press plate which is spring loaded towards an outfeed envelope support wall 819 to maintain opened (cut) envelopes 87 in a stacked and generally vertical orientation on outfeed platform 815. The infeed and outfeed platforms 809, 815 are shown connected by a generally narrow envelope travel path 820 along which mailpieces 87 (such as envelopes) are moved by a belt 821 operating in conjunction with a ski 822 biased toward belt 821 by a spring 823, as shown in FIG. 9.

Envelopes 87 retained on the infeed platform 809 are advanced by belt 821 past the generally horizontally oriented cutter wheels 803, 805 which cut portions of the bottom edges of the envelopes 87 as described in more detail below. As shown in FIG. 9, the cutter wheels 803, 805 have respective beveled edges 824, 825. The cutter wheels 803, 805 overlap to cut mailpieces 87 that are fed to the cutter wheels 803, 805. As the envelopes 87 are moved along travel path 820 they encounter a deflection wall 826 that deflects the envelopes 87 towards retainer 817 and an envelope stacker 827. The envelope stacker 827 is formed of a plurality of wheels 828, rotating in the direction of arrow 829, and having protrusions (not shown) with which each opened envelope 87 is urged by repetitive impacts against a stacking wall 831. In this manner opened envelopes 87, as they arrive, are maintained with their leading edges against wall 831 to stack sequentially until all mailpieces 87 at the infeed platform 809 have been opened. The infeed platform 809 is inclined downwardly towards wall 813 and has a slot 833 to enable a bracket (not shown) to support retainer 811 from below platform 809. Outfeed platform 815 is inclined downwardly away from wall 819 and provided with a slot 835 through which retainer 817 can be movably supported with a bracket 837. The spring loading of retainers 811, 817 is obtained with suitable springs mounted below platforms 809, 815 respectively.

An envelope jogger 839 is provided to urge the contents of envelopes 87 against one edge or side within the envelopes 87. The envelopes 87 are placed in a general vertical orientation on a platform 841 which is vibrated in a vertical direction in a conventional manner to bounce envelopes 87 up and down and thus urge their contents to move downwardly towards the bottom edge and to register the bottom edges of the mailpieces 87.

After completion of the jogging operation, the jogged and registered envelopes are then placed on infeed platform 809 with the edges, that are opposite from the edge where the contents were shifted to during jogging, facing down. The mailpieces 87 are fed to the cutter wheels 803, 805 where they are cut in a manner discussed in more detail below. As the mailpieces 87 are cut, any biological powder material falling off or out of the mailpieces 87 collects below the cutter wheels 803, 805 and in a chamber (not shown) contained within the housing 807 below the structure shown in FIG. 8. The ductwork 23 is connected through an opening 845 in communication with the chamber so that the biological powder material will be extracted through the ductwork 23 for analysis as previously discussed.

Figure 10:
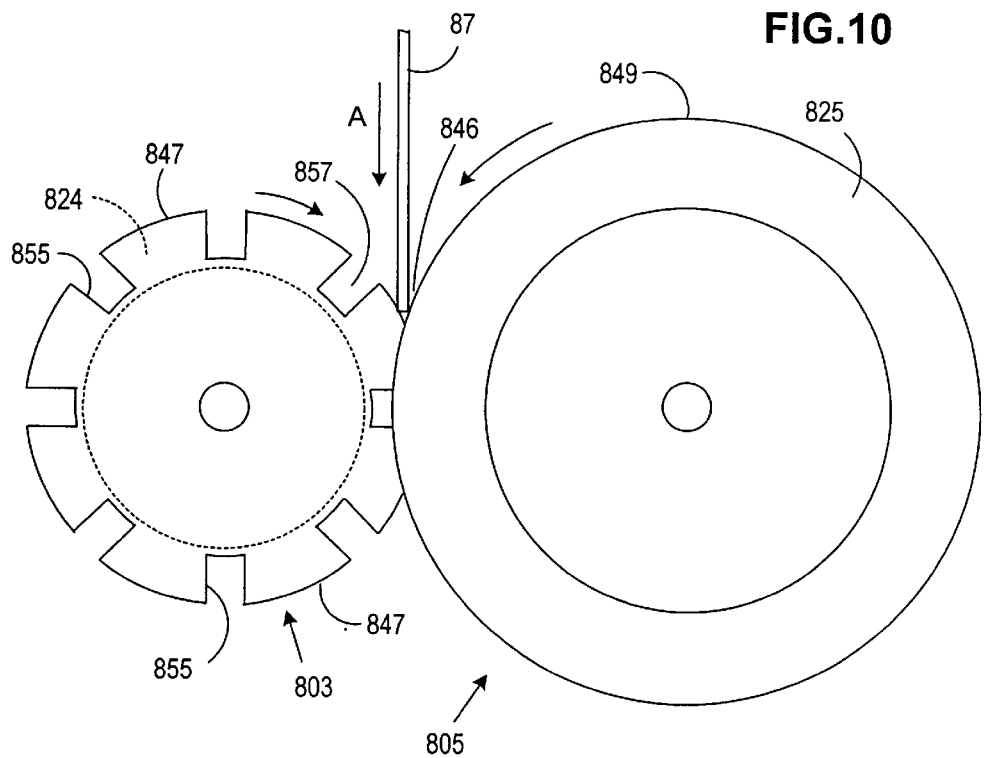
FIG. 10 is a top plan view of FIG. 9 showing only the cutter wheels and mailpiece orientation during cutting.
Figure 11:
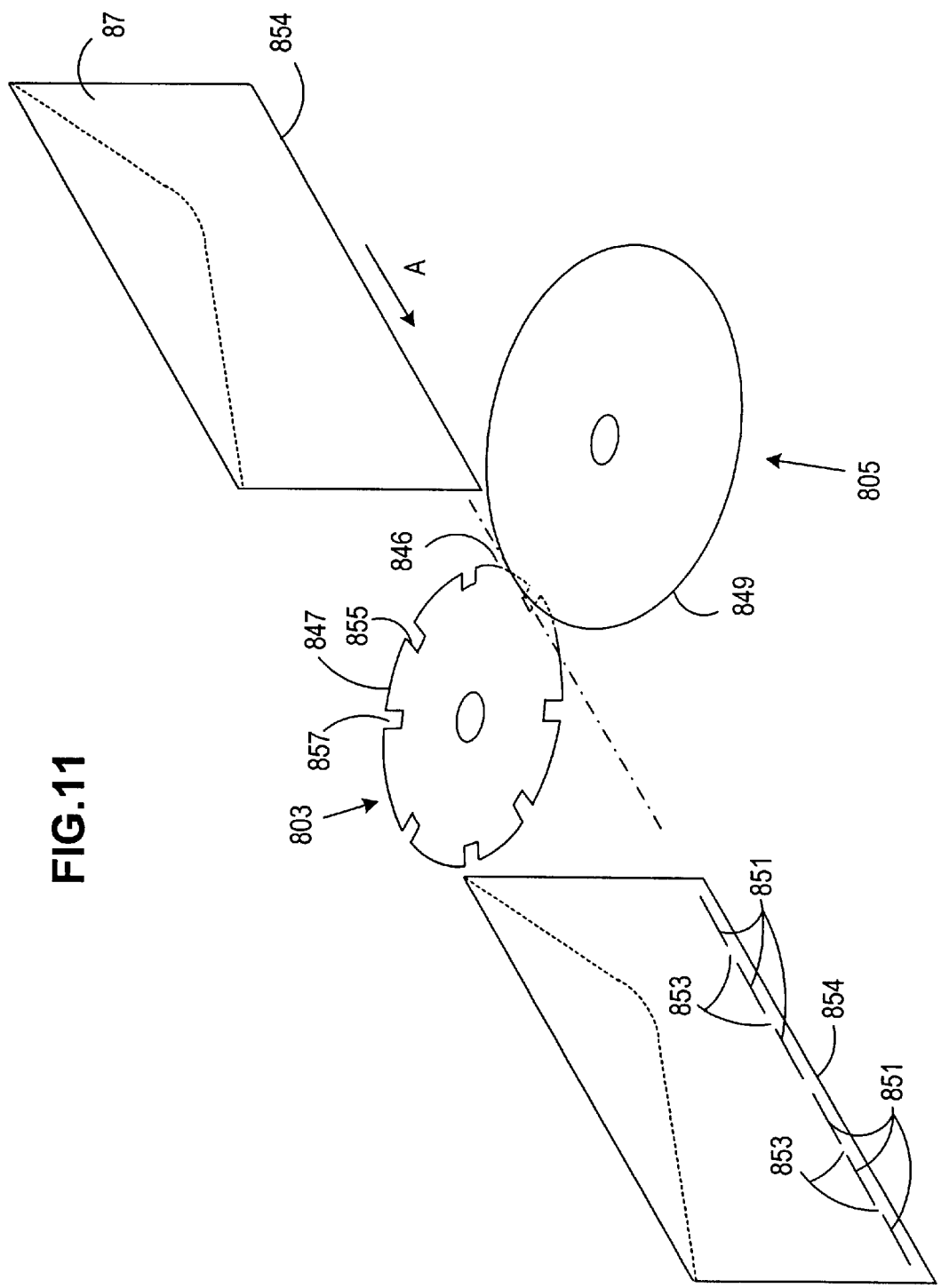
FIG. 11 is a schematic drawing showing the cutting of a mailpiece using the cutter wheels of FIG. 10.

Referring specifically to FIGS. 9–11, a first embodiment of the cutter wheels 803, 805 shall be discussed. Belt 821 is driven by a motor 843 via a pulley and belt system 844 and a shaft 845 in order to drive individual mailpieces 87 into a nip 846 defined between the cutting edges 847 and 849 of respective cutter wheels 803, 805. As belt 821 is driven, so is the cutting wheel 805 which is also mounted on shaft 845. The overlap of the cutting edges 847 and 849 also causes a rotation of cutter wheel 803 about a shaft 848. Accordingly, as the mailpieces 87 are fed along the arrow "A" into nip 846, the bottom of the mailpieces 87 is cut by the interaction of edges 847, 849 to produce the slots 851 shown in FIG. 11. The ability to produce the slots 851 is made by providing the cutter wheel 803 with notches 855 that are located around the perimeter of the cutter wheel 803. The notches 855 provide areas 857 of discontinuity in the cutting edge 847. It is the discontinuities 857 that produce corresponding uncut areas 853 in the mailpiece 87 while each section of the cutting edge 847 between two discontinuities 857 produces a single slot 851. It is to be noted that in prior art systems, such as that shown in U.S. Pat. No. 3,828,634 (which is hereby incorporated by reference) two cutting wheels are used that are similar to cutter wheel 805 in that the cutting edges extend around the perimeter in an unbroken manner. Thus, in the prior art the result was that an entire bottom edge of the envelope was completely removed opening the entire bottom of the envelope to permit the extraction of the envelope contents.

In the instant invention, while the slots 851 provide openings through which powder material can be expelled and tested in the detection system 101, the solid portions 853 remain intact so that the bottom edge 854 of the mailpiece 87 remains in place. Therefore, the contents inside the mailpiece 87 remain contained therein preserving the privacy of the contents and permitting the mailpiece 87 to be further processed for final delivery through the normal mail processing system if it is not contaminated. The plurality of slots 851 provide a greater amount of open area for the powder material to fall through as compared to the opening created at the corner of the mailpiece 87 by the corner snipper 13.

Figure 12:
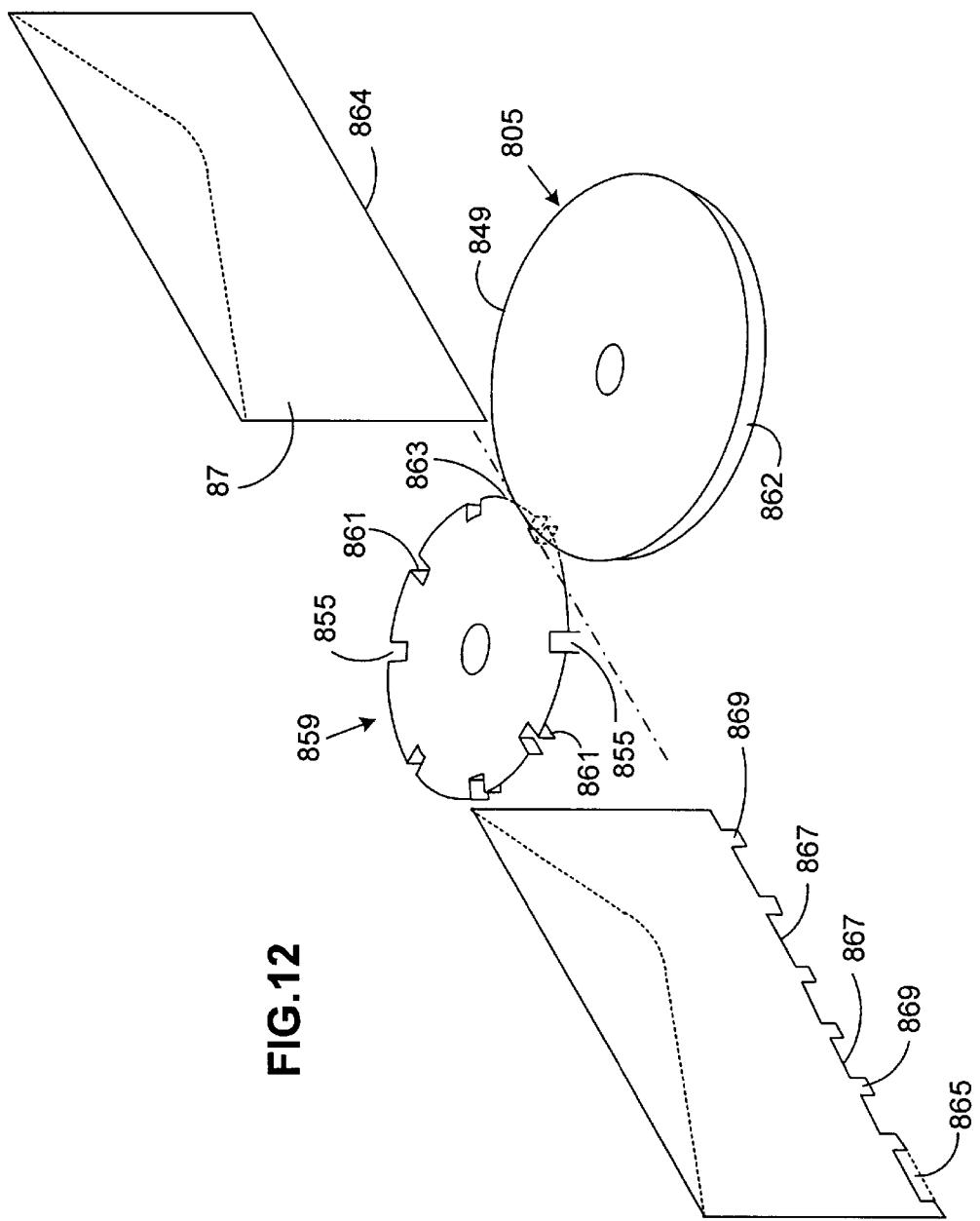
FIG. 12 is a schematic drawing showing the cutting of a mailpiece using a second embodiment of cutter wheels.

FIG. 12 shows a second embodiment where the cutter wheel 803 has been replaced by the cutter wheel 859. The cutter wheel 859 is similar to the cutter wheel 803 but further includes vertically extending cutting edges 861 at each side of the notches 855. Further, a circular urethane wheel 862 has been mounted on shaft 845 directly below cutter wheel 805 to rotate therewith. Accordingly, as the mailpieces 87 pass between a nip 863 the bottom of the mailpiece 87 is cut in a castellated appearance whereby a plurality of segments 865 of the lower edge 864 have been removed to produce a plurality of edge openings 867. The openings 867 allow any powder material to pass therethrough during the jogging and compression/decompression cycles while the uncut edge segments 869 retain the contents within the mailpiece 87. Once again, the opened area of the mailpieces 87 are significantly increased over a cut corner opening to allow more opportunity for powder material to escape during the jogging and compression/decompression cycles.

Additional advantages and modifications will readily occur to those skilled in the art. Therefore, the invention in its broader aspects is not limited to the specific details, and representative devices, shown and described herein. Accordingly, various modifications may be made without departing from the spirit or scope of the general inventive concept as defined by the appended claims. For example, the following are representative examples of such modifications:

1. The functions of the controller 81 and power supply 82 can be integrated in the jogger device 97 so that by pressing a single switch the entire jogging and compression/decompression cycles will automatically be executed. Moreover the jogging cycle can be initiated first with the compression/decompression cycles occurring during the jogging cycle.

2. The cutter wheel 803 can be modified to have any number of notches 855 and cutting edges 861 in order to vary the number of slots 851 and openings 867 that are made during cutting. Further, different notches can be of a different size to produce slots 851 and openings 867 of different sizes. Additionally, the notch can be sized to produce only a single larger slot 851 or opening 867.

3. The urethane wheel 862 can be made of other materials that provide a proper backing for cutting and which does not damage the cutting edges 861. Further, the urethane wheel can be integrated on the cutting wheel 805.

4. The cutter wheels of FIGS. 11 and 12 can be used alone separate from the mail opening device 801 for cutting the envelopes in the inventive manner. However, by using the mail opening system in conjunction therewith the initial jogging and the cutting features are integrated within a single unit.

5. While two specific air-monitoring tests are shown, only one may be implemented. Further, the invention contemplates any type of testing that can be performed on the expelled air to detect any type of contamination.

What is claimed is:

1. A method for expelling air out of mailpieces comprising the steps of:
creating a stack of the mailpieces;
cutting an opening in at least some of the mailpieces;
jogging the stack of mailpieces; and
subjecting the stack of mailpieces to at least one compression/decompression cycle during the jogging step thereby expelling air out of the at least some of the mailpieces through their corresponding openings.

2. A method as recited in claim 1, further comprising subjecting the stack of mailpieces to a plurality of the compression/decompression cycles during the jogging step.

3. A method as recited in claim 2, further comprising testing the expelled air to determine if the expelled air is contaminated.

4. A method as recited in claim 3, further comprising testing the expelled air to determine if the expelled is contaminated with biological agents.

5. A method as recited in claim 2, further comprising registering the stack of mailpieces prior to the cutting, jogging, and subjecting steps.

6. A method as recited in claim 5, further comprising registering the stack of mailpieces by vibrating the stack of mailpieces in a first jogger system and jogging the stack of mailpieces by vibrating them in a second jogger system having apparatus for performing the compression/decompression cycles.

7. A method as recited in claim 2, wherein the jogging step lasts approximately 1 minute.

8. A method as recited in claim 2, wherein the occurrences of the plurality of compression/decompression cycles are evenly spaced during the jogging step.

9. A method as recited in claim 5, wherein the registering and jogging steps are performed in a single jogger having apparatus for performing the compression/decompression cycles.

10. A method as recited in claim 1 wherein the compression/decompression cycle is a mechanical compression/decompression cycle.

11. A jogger system for a stack of mailpieces, the jogger system comprising:
 a jogger tray within which the stack of mailpieces is positioned;
 a jogger device that jogs the jogger tray; and
 means for subjecting the stack of mailpieces to a compression/decompression cycle, the subjecting means disposed within the jogger tray.

12. A jogger system as recited in claim 11, wherein the jogger tray includes first and second side walls, and wherein the subjecting means includes a paddle disposed and movable between the first and second side walls, and means for moving the paddle into contact with the stack of mailpieces to cause the mailpieces to be compressed between the paddle and the first side wall and for causing the paddle to retract from the stack of mailpieces to decompress the mailpieces.

13. A jogger system as recited in claim 12, wherein the moving means includes a controller that causes the paddle to move into contact with and retract from the stack of mailpieces a plurality of times during a predetermined period of time.

14. A jogger system as recited in claim 13, wherein the moving means further includes a motor, a lead screw, and a guide rod, and wherein the paddle is operatively connected to the lead screw and the guide rod, the motor is connected to the lead screw and is controlled by the controller such that as the motor is actuated by the controller it drives the lead screw whereby the paddle moves between the first and second side walls along the lead screw and the guide rod.

15. A jogger system as recited in claim 14, wherein the jogger tray includes a plate hingedly connected to the first side wall and a switch mounted on the first side wall behind the plate and in operative communication with the controller, and wherein at times when the paddle is moved into contact with the stack of mailpieces the stack of mailpieces contact and force the plate to move into contact with and activate the switch, the activated switch sends a signal to the controller, and the controller upon receipt of the signal causes the paddle to retract from the stack of mailpieces.

16. A jogger system as recited in claim 15, wherein the jogger tray includes a front wall, a rear wall, a cover hingedly connected to the rear wall to move between a closed position and an open position, and a platform upon which the stack of mailpieces is disposed and along which the paddle moves.

17. A jogger system as recited in claim 16, wherein at times when the cover is in the closed position the cover, the first and second side walls, the rear wall, and a top of the platform define a first chamber and a bottom of the platform, the first and second side walls, rear wall, and front wall define a second chamber below the first chamber.

18. A jogger system as defined in claim 17, wherein the platform is spaced from the rear wall creating an opening therebetween permitting air to flow between the first and second chambers.

19. A jogger system as recited in claim 18, wherein the jogger tray has means for connecting the second chamber to a vacuum source such that at times when the vacuum source is connected to the jogger tray air is removed from the first and second chambers.

20. A jogger system as recited in claim 11 wherein the compression/decompression cycle means is a mechanical compression/decompression cycle means.

* * * * *